United States Patent [19]

Colling

[11] Patent Number: 5,314,858
[45] Date of Patent: May 24, 1994

[54] VINYL ACETATE CATALYST PREPARATION METHOD

[75] Inventor: Philip M. Colling, Corpus Christi, Tex.

[73] Assignee: Hoechst Celanese Corporation, Somerville, N.J.

[21] Appl. No.: 961,739

[22] Filed: Oct. 14, 1992

[51] Int. Cl.$^5$ .................. B01J 37/03; B01J 23/44; B01J 23/52
[52] U.S. Cl. .................. 502/330; 502/300; 502/439
[58] Field of Search .............. 502/330, 243, 170, 439, 502/300, 240

[56] References Cited

U.S. PATENT DOCUMENTS

| | | | |
|---|---|---|---|
| 3,743,607 | 7/1973 | Sennewald et al. | 502/170 |
| 3,775,342 | 11/1973 | Kronig et al. | 502/170 |
| 3,822,308 | 7/1974 | Kronig et al. | 560/245 |
| 4,048,096 | 9/1977 | Bissot et al. | 502/170 |
| 4,087,622 | 5/1978 | Nakamura et al. | 502/179 X |
| 4,370,261 | 1/1983 | Wunder et al. | 502/328 |
| 4,902,823 | 2/1990 | Wunder et al. | 560/245 |
| 5,189,004 | 2/1993 | Bartley | 502/170 |

FOREIGN PATENT DOCUMENTS

| | | | |
|---|---|---|---|
| 0464633A1 | 1/1992 | European Pat. Off. | |
| 52-018154 | 5/1977 | Japan | 502/170 |
| 1521652 | 8/1978 | United Kingdom | |

OTHER PUBLICATIONS

Davidson, J. M. et al. "Selectivity Problems and Kinetic Models in the Palladium Catalysed Oxidation of Ethene and Acetic Acid to Ethenyl Acetate. Related Reactions of Propene, 1-Butene and 1-Hexene." *Front. Chem. React. Eng. [Proc.-Int. Chem. React. Eng. Conf.]* vol. 1, 300-313, Wiley, N.Y. 1984

Primary Examiner—Helen M. S. Sneed
Assistant Examiner—Douglas J. McGinty
Attorney, Agent, or Firm—Donald R. Cassady; Stuart D. Frenkel

[57] ABSTRACT

A method of preparing a catalyst particularly useful in the reaction of ethylene, oxygen and acetic acid in the vapor phase to form vinyl acetate comprises impregnating a porous support with water soluble salts of palladium and gold, fixing the palladium and gold on the support as water insoluble compounds by contacting the salt-impregnated support with a reactive solution in two separate fixing stages wherein the treated support is dried and allowed to stand prior to treatment in the second stage to precipitate the insoluble compounds on the support and reducing the insoluble compounds to free palladium and gold. The catalysts prepared in this manner have been shown to provide improvement with respect to reduced selectivity to $CO_2$ during the vinyl acetate forming reaction.

12 Claims, No Drawings

VINYL ACETATE CATALYST PREPARATION METHOD

BACKGROUND OF THE INVENTION

1. Field of the Invention

The present invention relates to a novel method of producing a catalyst useful in the reaction of ethylene, oxygen and acetic acid in the vapor phase to form vinyl acetate. In particular, the present invention is directed to a novel method of forming a catalyst useful in the catalytic formation of vinyl acetate in which said catalyst comprises metallic palladium and gold deposited on a suitable porous support.

2. Description of the Prior Art

It is known in the art that vinyl acetate can be produced by reacting ethylene, oxygen, and acetic acid in the gaseous phase and in the presence of a catalyst comprising palladium, gold and an alkali metal acetate supported on certain carrier materials such as silica. Generally, such catalyst system exhibits a high activity. Unfortunately, results utilizing such palladium and gold catalysts have been inconsistent. This inconsistency appears to be based somewhat on the distribution pattern or profile of the catalyst components which are deposited on and in relation to the support. For example, when use is made of the known vinyl acetate catalyst systems comprising a porous support with palladium and gold, the metal components deposited at or about the support interiors or central regions do not contribute significantly to the reaction mechanism, since the reactants are not readily able to diffuse into the central or inner regions of the porous network of the catalyst. Hence, the reaction occurs substantially only at the outermost or surface regions of the catalyst. The catalyst components in the interior regions of the support do not largely contribute to the reaction scheme, resulting in a reduction in catalytic efficiency per unit weight of the catalyst components. Furthermore, the use of a highly active catalyst at times gives rise to side reactions and, therefore, leads to a reduced selectivity to vinyl acetate.

Various patents have been granted based on the desire to more evenly distribute and anchor the gold and palladium catalytic components within a narrow band on the support surface to provide a vinyl acetate catalyst having high yield, good selectivity and long life. Examples of such patents include U.S. Pat. Nos. 4,087,622; 4,048,096; 3,822,308; 3,775,342 and British Patent 1,521,652.

The basic method of forming the vinyl acetate catalyst containing palladium and gold deposited on a catalyst support comprises (1) impregnating the support with aqueous solutions of water-soluble palladium and gold compounds, (2) precipitating water-insoluble palladium and gold compounds on the catalyst support by contacting the impregnated catalyst support with a solution of compounds capable of reacting with the water-soluble palladium and gold compounds to form the insoluble precious metal compounds (3) washing the treated catalyst with water to remove anions which are freed from the initially impregnated palladium and gold compounds during precipitation and (4) converting the water-insoluble palladium and gold compounds to the free metal by treatment with a reducing agent. A final treatment usually involves (5) impregnating the reduced catalyst with an aqueous alkali metal acetate solution and (6) drying the final catalyst product.

Prior art attempts to provide a uniform distribution of the palladium and gold metals on the support has involved some manipulation of the above mentioned steps and/or by using support materials having various specified pore dimensions.

It is an object of the present invention to provide a method of preparing a vinyl acetate catalyst which contains palladium and gold on a porous support in which the fixing of the water soluble precious metal compounds as water insoluble compounds on the support can be achieved by contacting the impregnated support with sufficient reactive compound to insure complete precipitation and fixing of the precious metal compounds onto the support in multiple fixing steps.

SUMMARY OF THE INVENTION

It has now been found that particularly active supported catalysts containing palladium and gold useful for the production of vinyl esters from ethylene, lower carboxylic acids with 2-4 carbon atoms and oxygen in the gas phase at elevated temperature and at normal or elevated pressure can be obtained by manipulating step (2) of the process as described above. Typically, during the precipitation step (2), the impregnated catalyst support is impregnated with a solution of the reactive compound and then allowed to stand for over 16 hours to complete precipitation of the insoluble precious metal compounds. Typically, an excess of the reactive compound is utilized to insure that all of the soluble precious metal compounds are precipitated as insoluble compounds fixed to the catalyst support. The excess is generally about 120% or more of the amount needed to react with all of the precious metal compounds which have been impregnated onto the support. It has been desired to reduce the amount of reactive compound in the fixing solution which is contacted with the impregnated support as it has been found that better catalyst performance is achievable. Unfortunately, as stated above, if the water soluble precious metal compounds are not precipitated and thus fixed on the catalyst support, these compounds will wash from the support during the washing stage to remove the freed anion from the initially impregnated support.

To overcome this problem and in accordance with the present invention, a useful catalyst is formed by (1) simultaneously or successively impregnating a catalyst support with aqueous solutions of palladium and gold salts such as sodium-palladium chloride and auric chloride, (2) fixing the precious metals on the support by precipitating water-insoluble palladium and gold compounds by treatment of the impregnated supports with a reactive basic solution such as aqueous sodium hydroxide which reacts to form hydroxides of palladium and gold on the support surface, (3) washing with water to remove the chloride ion (or other anion), and (4) reducing the precious metal hydroxides to free palladium and gold, wherein the improvement comprises during fixing step (2) utilizing two separate precipitation stages wherein the amounts of the reactive compound in contact with the salt-impregnated support in each stage is no more than that required to react with the water soluble precious metal compounds impregnated in the support. Between the separate fixing or precipitation stages, the support which has been impregnated with the reactive basic solution is allowed to stand for a set period of time to allow precipitation of the water insoluble precious metal compounds before the second fixing stage in which additional reactive basic compound is added to the support. While the overall amount of the reactive compound added to the support is in excess of that required to react with all the precious metal compounds which are present as water soluble salts, it has been found that by dividing the fixing into at least two stages smaller amounts of the reactive compound can be reacted with the water soluble precious metal salts in each stage. This achieves the desire to limit the amount of the reactive compound coming in contact with the salt-impregnated support at one time and still insures that the support is eventually contacted with a sufficient amount of reactive compound to fix all of the water soluble precious metal salts as water insoluble precious metal compounds so as to anchor or fix the precious metals on the support.

DETAILED DESCRIPTION OF THE INVENTION

In the preparation of the improved catalyst of the present invention, a suitable catalyst support is first impregnated with an aqueous solution containing water-soluble palladium and gold compounds. Separate solutions of palladium and gold compounds could also be used successively, but it is less convenient to proceed in that fashion. Palladium (II) chloride, sodium palladium (II) chloride and palladium (II) nitrate are examples of suitable water-soluble palladium compounds, whereas auric (III) chloride or tetrachloroauric (III) acid and the alkali metal salts thereof can be used as the water-soluble gold compounds. The generally available tetrachloroauric (III) acid and the sodium palladium (II) chloride are preferred because of their high water solubility. Typically, the quantity of these compounds employed is such as to provide 1 to 10 grams of palladium and 0.5 to 5 grams of gold per liter of finished catalyst. Accordingly, the amount of gold present in the catalyst will be from about 10 to about 70% of the amount of palladium. The amount of gold and palladium contained on the support is not believed to be critical to the method of preparation as catalysts formed by the "double-fixing" method of this invention with varied amounts of each precious metal will yield similar improved results during the formation of vinyl acetate. Thus, catalysts containing even higher or lower amounts of the precious metals relative to that recited above could be useful in the formation of vinyl acetate by reaction of ethylene, oxygen and acetic acid in the vapor phase as long as the catalyst is formed by the novel method set forth herein. The volume of solution used for impregnating the support with the precious metals is important. For effective deposition, the volume of the impregnating solution should be from 95 to 100% of the absorptive capacity of the catalyst support and preferably it should be 98-99%.

The support material for the catalyst according to the present invention can be of any diverse geometrical shape. For example, the support can be shaped as spheres, tablets or cylinders. The geometrical dimensions of the support material can, in general, be in the range of 1-8 mm. A most suitable geometrical shape is, in particular, the spherical shape, for example, spheres with diameters in the range of 4-8 mm. These supports are generally called pills.

The specific surface area of the support material can vary within wide limits. For example, support materials which have an inner surface area of 50-300 m$^2$/g and especially 100-200 m$^2$/g (measured according to BET) are suitable.

Examples of support materials which can be used include silica, aluminum oxide, aluminum silicates or spinels. Silica is the preferred support material.

After impregnation of the support with the water soluble palladium and gold compounds, the impregnated supports are dried prior to fixing the palladium and gold compounds as water insoluble compounds on the support. The fixing solution is one which comprises an alkaline solution, for example, an aqueous solution which contains alkali metal hydroxides, alkali metal bicarbonates and/or alkali metal carbonates. It is particularly preferred to use aqueous solutions of sodium hydroxide or potassium hydroxide. By treatment with the alkaline solution, the precious metal salts are converted to water insoluble compounds believed to be hydroxides and/or oxides, at least in the case where the alkaline solution is a solution of sodium hydroxide or potassium hydroxide.

According to the prior art, the alkaline fixing solution was simply poured onto the impregnated supports and the treated supports were allowed to stand for up to 24 hours or more during the precipitation. The volume of fixing solution was that equal to the dry absorptivity of the support and the amount of alkaline compound used was in excess on a molar basis of that required to react with all of the impregnated precious metal salts. It has now been found that catalyst activity such as for the formation of vinyl acetate can be maintained and that the side reaction relative to the formation of carbon dioxide can be substantially reduced if the fixing step (2) is divided into at least two separate stages of treatment with the alkaline fixing solution. In each separate fixing treatment, the amount of the alkaline reactive compound is no more than that equal to the molar amount required to react with all of the precious metal compound which is present on the support as a water soluble compound. Preferably, the amount of reactive compound used in each fixing stage is less than the molar amount required to react with all of the water soluble precious metal compound. The first fixing stage is conducted by impregnating the dried, impregnated support with the alkaline fixing solution in an amount equal to about the dry absorptivity of the support. The amount of the alkaline compound contained in solution should be such that the ratio of alkali metal to anion from the water soluble precious metal salt be from about 0.7:1 to about 1:1 molar and the volume should equal the dry support absorptivity. The second fixing stage is conducted by adding the undried partially fixed pills to a second portion of aqueous fixing solution. In this solution the ratio of alkali metal to anion from the precious metal salt should be from about 0.2:1 to about 0.9:1 molar. The volume of solution should cover the pills. Preferably, the total amount of alkali metal to anion should range from about 1.1:1 to about 1.6:1 molar for the combined fixing step. Subsequent to treatment in the first fixing stage, the treated supports are allowed to stand for a sufficient period of time to allow precipitation of the insoluble precious metal compounds. The period of time will vary but typically will range from about 2 hours to 8 hours before the support is again treated with the second portion of alkaline fixing solution. Subsequent to treatment in the second fixing stage, the treated supports are allowed to stand again for at least an additional 2 hours, preferably, at least 4 hours and may stand to complete precipitation for up to about 16 hours.

The treatment in the second fixing stage can be equivalent to that of the first stage wherein the treated dried and partially fixed supports are impregnated with the fixing solution at the desired alkaline concentration. The total volume of solution is sufficient to cover the volume of the support. Alternatively, the support can be impregnated in the second fixing stage by a process designated "rotation immersion" which is set forth in copending, commonly assigned application Ser. No. 07/961,738, allowed. In this process, the once-fixed catalysts are immersed in the alkaline fixing solution and tumbled or rotated therein during the initial stages of the precipitation of the water insoluble precious metal compounds. The rotation or tumbling of the supports in the alkaline fixing solution should proceed for at least 0.5 hour upon the initial treatment and, preferably, for at least 1 hour. The rotation immersion treatment can last as long as up to 4 hours before the treated supports are allowed to stand in the fixing solution to insure that complete precipitation of the water soluble precious metal compounds take place.

Any type of rotation or tumbling equipment can be used as the exact apparatus utilized is not critical. What may be critical, however, is the extent of the rotating motion. Thus, the rotation should be sufficient so that all surfaces of the impregnated supports are evenly contacted with the alkaline fixing solution. The rotation should not be so harsh that actual abrasion of the insoluble precious metal compounds takes place such that the insoluble compounds are abraded off the support surface. Generally, the extent of rotation should be about 1 to 10 rpm and possibly even higher depending upon the exact support utilized and the amount of precious metal to be deposited on the support. The rpm to be used is variable and may also depend upon the apparatus utilized, the size and shape of the support, the type of support, metal loadings, etc., but should fall within the guidelines expressed above that while a small amount of abrasion may take place, it is not to be such that the insoluble compounds are actually abraded off the support surface to an unacceptable degree.

Subsequent to the fixing and precipitation step, the supports are washed such as with distilled water so as to remove the anions, such as the chlorides, which are still contained on the support and freed from the initial impregnating solution. Washing is continued until all of the anions are removed from the support. No more than about 1,000 ppm of anion should remain on the catalyst. To ensure substantially complete removal of the anions such as chloride ion from the catalyst, the wash effluent can be tested with silver nitrate. The catalyst is then dried at temperatures not to exceed about 150° C. under an inert atmosphere such as a continuous nitrogen or air flow.

The fixed and washed material is then treated with a reducing agent in order to convert the precious metal salts and compounds which are present into the metallic form. The reduction can be carried out in the liquid phase, for example, with aqueous hydrazine hydrate, or in the gas phase, for example, with hydrogen or hydrocarbons, for example, ethylene. If the reduction is carried out with a solution of hydrazine hydrate, the reaction is preferably carried out at normal temperature. When the reduction is carried out in the gas phase, it can be advantageous to carry out the reaction at elevated temperature, for example, at 100°-200° C. in the case of reduction with ethylene. The reducing agent is appropriately employed in excess so that it is certain that all of the precious metal salts and compounds are converted into the metallic form.

Depending on the use for which the catalyst prepared in this way is intended, the latter can also be provided with customary additives. Thus, for example, additions of alkali metal acetates are advantageous when the catalyst is to be used for the preparation of unsaturated esters from olefins, oxygen and organic acids. In this case, for example, the catalyst can, for this purpose, be impregnated with an aqueous solution of potassium acetate and then dried.

The catalysts according to the invention can be used with particular advantage in the preparation of vinyl acetate from ethylene, oxygen and acetic acid in the gas phase. For this purpose, those catalysts according to the invention which contain silica as the support material and additives of alkali metal acetates are particularly suitable. In the above mentioned preparation of vinyl acetate, such catalyst are also distinguished by high activity and selectivity and by long life.

EXAMPLES 1-7

The catalysts of Examples 1-7 were prepared in accordance with the method of the present invention. For each example, silica catalysts supports provided by Sud Chemie having a spherical shape and a diameter of 7.3 mm were utilized unless otherwise specified. In all the examples, 250 cc. of the supports were impregnated with the same aqueous solution containing sodium palladium chloride and tetrachloroauric acid. The supports were dried in hot air at a temperature not exceeding 100° C. The treated supports were impregnated with an aqueous solution of sodium hydroxide. The amount of sodium hydroxide used in each of the fixing stages is set forth in Table 1 as the molar ratio of sodium to chloride anion. The volume of the sodium hydroxide solution was equal to the dry support absorptivity in the first fixing stages. After the first stage, the base treated support was allowed to stand for 4 hours and then subsequently poured into the second sodium hydroxide solution. Subsequent to the second treatment, the base treated material was allowed to stand for an additional about 16 hours. Variations in the fixing times are also set forth in Table 1. After fixing, the base treated material was thoroughly washed with distilled water to remove the chloride ions to accepted levels which were at most 1,000 ppm chloride. The water flow rate was about 200 cc/min for approximately 5 hours. The catalyst was dried under a continuous nitrogen flow at a temperature of no more than 150° C. The dried catalysts were reduced with ethylene at a temperature of 150° C. The reducing gas contained 5% ethylene in nitrogen and was passed over the catalysts for 5 hours at atmospheric pressure. The reduced catalyst was impregnated with an aqueous solution containing 10 grams of potassium acetate at a solution volume equal to the support absorptivity. The catalysts were dried at a temperature no greater than 150° C.

The catalysts were utilized to prepare vinyl acetate by the reaction of ethylene, oxygen and acetic acid according to methods well known in the art.

TABLE 1

| Example | Support Size mm. | Pd g/l | Au g/l | First Precipitation | | | Second Precipitation | | |
|---|---|---|---|---|---|---|---|---|---|
| | | | | Time hrs. | Volume ml | Na/Cl ratio | Time hrs. | Volume ml | Na/Cl ratio |
| 1 | 7 | 6.6 | 3.0 | 4 | 90 | 1/1 | >16 | 134 | 0.3/1 |
| 2 | 5 | 6.6 | 3.0 | 4 | 89 | 1/1 | >16 | 134 | 0.3/1 |
| 3 | 7 | 6.6 | 3.0 | 4 | 90 | 0.8/1 | >16 | 134 | 0.5/1 |
| 4 | 7 | 6.6 | 3.0 | 4 | 87 | 0.7/1 | >16 | 134 | 0.6/1 |
| 5 | 7 | 6.6 | 3.0 | 4 | 90 | 1/1 | >16 | 134 | 0.6/1 |
| 6 | 7 | 6.6 | 3.0 | 4 | 87 | 0.8/1 | 15.5 | 134 | 0.8/1 |
| 7 | 7 | 6.6 | 3.0 | 4 | 87 | 0.8/1 | 4 | 134 | 0.8/1 |

What is claimed is:

1. In a method of preparing a catalyst composed of a porous support containing thereon precious metals comprising; impregnating said support with water soluble compounds of said precious metals, converting said water soluble precious metal compounds to water insoluble precious metal compounds by contacting said impregnated support with a water soluble compound to precipitate an insoluble precious metal compound on said support, and reducing said water insoluble precious metal compounds with a reducing gas to form free precious metals on said support, the improvement which comprises converting the precious metal to an insoluble precious metal compound in two steps, a first fixing stage with a solution containing a compound reactive with said water soluble precious metal compounds to precipitate on said support said water insoluble precious metal compounds, then contacting said supports with additional solution containing a compound reactive with said water soluble compounds in a second fixing stage to further precipitate on said support said water insoluble precious metal compounds.

2. The method of claim 1 wherein said precious metals comprise a mixture of soluble salts of palladium and gold.

3. The method of claim 2 wherein said soluble gold salt is present in an amount of 10 to 70% by weight of said soluble palladium salt.

4. The method of claim 2 wherein said treated support is allowed to stand for at least 4 hours subsequent to contact with said reactive solution in each of said fixing stages.

5. The method of claim 1 wherein said reactive compound is an alkaline compound.

6. The method of claim 5 wherein said alkaline compound comprises potassium or sodium hydroxide.

7. The method of claim 5 wherein the total amount of said alkaline compound contacted with said impregnated support equals a molar excess relative to the amount required to convert all of said water soluble precious metal compounds to said precious metal water insoluble compounds.

8. The method of claim 5 wherein said water soluble precious metal compounds are salts and said alkaline compound is present in an amount in said first fixing stage such that the molar ratio of alkali metal of said alkaline compound to anion from said salt is from about 0.7:1 to 1:1 and in an amount in said second fixing stage such that the molar ratio of alkali metal of said alkaline compound to anion from said salt is from about 0.2:1 to 0.9:1.

9. The method of claim 8 wherein the total amount of said alkaline compound contacted with said impregnated support in both of said fixing stages is such that the molar ratio of alkali metal of said alkaline compound to anion from said salt is from about 1.1:1 to 1.6:1.

10. The method of claim 9 wherein the amount of said alkaline compound in each of said first and second fixing stages is such that the molar ratio of alkali metal of said alkaline compound to anion from said salt is about 0.8:1.

11. The method of claim 1 wherein the volume of said reactive solution contacted with said impregnated support in each of said first fixing stage is equal to the dry absorptivity of said support.

12. The method of claim 1 wherein the volume of said reactive solution contacted with said impregnated support in said second fixing stage is sufficient to cover the volume support.

* * * * *